United States Patent
Gong et al.

(10) Patent No.: US 7,607,083 B2
(45) Date of Patent: Oct. 20, 2009

(54) TEST SUMMARIZATION USING RELEVANCE MEASURES AND LATENT SEMANTIC ANALYSIS

(75) Inventors: Yihong Gong, Sunnyvale, CA (US); Xin Liu, Berkeley, CA (US)

(73) Assignee: NEC Corporation, Tokyo (JP)

( * ) Notice: Subject to any disclaimer, the term of this patent is extended or adjusted under 35 U.S.C. 154(b) by 779 days.

(21) Appl. No.: 09/817,591

(22) Filed: Mar. 26, 2001

(65) Prior Publication Data

US 2002/0138528 A1 Sep. 26, 2002

Related U.S. Application Data

(60) Provisional application No. 60/254,535, filed on Dec. 12, 2000.

(51) Int. Cl.
G06F 17/00 (2006.01)
(52) U.S. Cl. .............................. 715/254; 705/3; 705/4; 705/5; 707/101; 707/102; 704/245
(58) Field of Classification Search ................ 715/530, 715/532, 526, 531; 704/1; 706/45; 707/3, 707/5; 725/116
See application file for complete search history.

(56) References Cited

U.S. PATENT DOCUMENTS

| | | | | |
|---|---|---|---|---|
| 6,029,195 | A * | 2/2000 | Herz ......................... | 725/116 |
| 6,356,864 | B1 * | 3/2002 | Foltz et al. ...................... | 704/1 |
| 6,523,026 | B1 * | 2/2003 | Gillis ............................ | 707/3 |
| 6,611,825 | B1 * | 8/2003 | Billheimer et al. ............ | 706/45 |
| 6,865,572 | B2 * | 3/2005 | Boguraev et al. .............. | 707/5 |
| 2002/0002450 | A1 * | 1/2002 | Nunberg et al. ................ | 704/1 |
| 2002/0078090 | A1 * | 6/2002 | Hwang et al. ............... | 707/513 |

FOREIGN PATENT DOCUMENTS

JP 2001-014341 A 1/2001

OTHER PUBLICATIONS

Goldstein et al. "Summarizing Text Documents: Sentence Selection and Evaluation Metrics" published Aug. 1999 by ACM Press pp. 121-128.*

(Continued)

*Primary Examiner*—Doug Hutton
*Assistant Examiner*—Quoc A Tran
(74) *Attorney, Agent, or Firm*—Sughrue Mion, PLLC

(57) ABSTRACT

Text summarizers using relevance measurement technologies and latent semantic analysis techniques provide accurate and useful summarization of the contents of text documents. Generic text summaries may be produced by ranking and extracting sentences from original documents; broad coverage of document content and decreased redundancy may simultaneously be achieved by constructing summaries from sentences that are highly ranked and different from each other. In one embodiment, conventional Information Retrieval (IR) technologies may be applied in a unique way to perform the summarization; relevance measurement, sentence selection, and term elimination may be repeated in successive iterations. In another embodiment, a singular value decomposition technique may be applied to a terms-by-sentences matrix such that all the sentences from the document may be projected into the singular vector space; a text summarizer may then select sentences having the largest index values with the most important singular vectors as part of the text summary.

20 Claims, 2 Drawing Sheets

OTHER PUBLICATIONS

Furnas et al. "Information Retrieval using a Singular Value Decomposition Model of Latent Semantic Structure" Published 1988 by ACM Press pp. 465-480.*

Goldstein et al. "Multi-Document Summarization By Sentence Extraction" published Apr. 2000 by ACM Press pp. 40-48.*

William W. Cohen "Data Integration Using Similarity Joins and a Word-Based Information Representation Language" By At& T Lab-Research, Shannon Laboratory, Published by ACM, vol. 18; No. 3, Jul. 2000, pp. 288-321.*

Chang et al., "Next generation content representation, creation and search for new media applications in education," *IEEE Proceedings, special issue on Multimedia Signal Processing*, vol. 86, pp. 884-904 May 1998.

Baldwin et al., "Dynamic coreference-based summarization" in *Proceedings of the Third Conference on Empirical Methods in Natural Lanuage Processing (EMNLPS)*, (Granada, Spain), Jun. 1998.

Sanderson, "Accurate user directed summarization from existing tools," in *Proceedings of the 7th International Conference on Information and Knowledge Management (CIKM98)*, 1998.

Hovy et al., "Automated text summarization in SUMMARIST," in *Proceedings of the TIPSTER Workshop*, (Baltimore, MD), 1998. http://www.SRA.com.

Buckley et al., "The smart/empire TIPSTER IR system," in *Proceedings of TIPSTER Phase III Workshop*, 1999.

Goldstein et al., "Summarizing text documents: Sentence selection and evaluation metrics,"in *Proceedings of ACM SIGIR '99*, (Berkeley, CA), Aug. 1999.

Dumais, "Improving the retrieval of information from external sources," *Behavior Research Methods, Instruments, and Computers*, vol. 23, 1991.

Press et al., *Numerical Recipes in C: The Art of Scientific Computing*, Cambridge, England: Cambridge University Press, 2 ed., 1992.

Deerwester et al., "Indexing by latent semantic analysis," *Journal of the American Society for Informatio Science*, vol. 41, pp. 391-407, 1990.

Berry et al., "Using linear algebra for intelligent information retrieval," Tech. Rep. UT-CS-94-270, University of Tennessee, Computer Science Department, Dec. 1994.

Berger et al., "A maximum entropy approach to natural language processing," *Journal of Computational Linguistics*, vol. 22, 1996.

Japanese Patent Application Publication No. 6-215049, published Aug. 5, 1994.

Japanese Patent Application Publication No. 9-319768, published Dec. 12, 1997.

Japanese Patent Application Publication No. 11-102372, published Apr. 13, 1999.

Japanese Patent Application Publication No. 11-259521, published Sep. 24, 1999.

Hirao, Tsutomu: Abstracting of texts based on importance of terms. Journal of Information Processing, Japan, Information Processing Society of Japan, May 15, 1998, vol. 98, No. 34, p. 41-47.

* cited by examiner

TEST SUMMARIZATION USING RELEVANCE MEASURES AND LATENT SEMANTIC ANALYSIS

This application claims the benefit of U.S. Provisional Application No. 60/254,535, filed Dec. 12, 2000, entitled "Text Summarization Using IR Technique And Singular Value Decomposition," the disclosure of which is hereby incorporated by reference.

BACKGROUND OF THE INVENTION

1. Field of the Invention

The present invention is related generally to summarization of document contents, and more particularly to a system and method of summarizing the content of text documents through implementation of relevance measurement technologies and latent semantic analysis techniques.

2. Description of the Related Art

The explosive growth of the World-Wide Web has dramatically increased the speed and the scale of information dissemination. With a vast sea of accessible text documents now available on the Internet, conventional Information Retrieval (IR) technologies have become more and more insufficient to find relevant information effectively. Recently, it has become quite common that a keyword-based search on the Internet returns hundreds (or even thousands) of hits, by which the user is often overwhelmed. There is an increasing need for new technologies which assist users in sifting through vast volumes of information, and which can quickly identify the most relevant documents.

Given a large volume of text documents, presenting the user with summaries of these documents greatly facilitates the task of finding documents containing desired information. Text search and text summarization are two essential technologies that complement each other. Conventional text search engines return a set of documents based upon a relevance measurement with respect to a keyword query, for example; text summarization systems may then produce document summaries that facilitate a quick examination of the contents of each text document returned by the search (by providing, for example, an overview, keyword summary, or abstract).

In other words, a text search engine may typically serve as an information filter for identifying an initial set of relevant documents, while a cooperating text summarization system may serve as an information spotter for assisting the user in identifying a final set of desired or relevant documents.

There are two types of text summaries: generic summaries, and query-relevant summaries. Generic summaries provide an overall sense of a particular document's content, while query-relevant summaries present only content from a particular document that is closely related to the initial search query.

A good generic summary should contain the main topics presented in a document while minimizing redundancy. Since the generic summarization process is not responsive to a particular keyword query or topic search, developing a high quality generic summarization method and system has proven very challenging. A query-relevant summary, on the other hand, presents document contents that are specifically related to an initial search query; in many existing systems, creating a query-relevant summary is essentially a process of retrieving query-relevant sentences from the document. It will be appreciated by those of skill in the art that this process is strongly related to the text retrieval process. Accordingly, query-relevant summarization is most often achieved simply by extending conventional IR technologies.

Many text summarization methods have been proposed; many recent research studies have been directed toward query-relevant text summarization methods. For example, B. Baldwin and T. S. Morton have proposed a query-sensitive summarization method that selects sentences from the documents until all the phrases in the query are represented. A sentence in the document is considered to represent a phrase in the query if the sentence and the phrase "co-refer" to the same individual, organization, event, and so forth (B. Baldwin et al., *Dynamic Co-reference-Based Summarization*, in Proceedings of the Third Conference on Empirical Methods in Natural Language Processing (EMNLP3), Granada, Spain, June 1998). R. Barzilay and M. Elhadad have developed a method that creates text summaries by finding lexical chains in documents (R. Barzilay et al., *Using Lexical Chains For Text Summarization*, in Proceedings of the Workshop on Intelligent Scalable Text Summarization (Madrid, Spain), August 1997).

Mark Sanderson has approached the problem by dividing each document into equally sized overlapping passages, and using the INQUERY IR system to retrieve the passage from each document that best matches a query. This "best passage" is then used as a summary of the document. A query expansion technique called Local Context Analysis (LCA, which is also from INQUERY) is used before the best passage retrieval. Given a topic and a document collection, the LCA procedure retrieves top-ranked documents from the collection and examines the context surrounding the topic terms in each retrieved document; LCA then selects the words or phrases that are frequent in these contexts and adds these words or phrases to the original query (M. Sanderson, *Accurate User Directed Summarization From Existing Tools*, in Proceedings of the 7th International Conference on Information and Knowledge Management (CIKM98), 1998).

The SUMMARIST text summarizer from the University of Southern California attempts to create text summaries based on the equation:

summarization=topic identification+interpretation+generation

The identification stage filters the input document to determine the most important central topics. The interpretation stage clusters words and abstracts them into some encompassing concepts. Finally, the generation stage generates summaries either by outputting some portions of the input, or by creating new sentences based on the interpretation of the document concepts (E. Hovy et al., *Automated Text Summarization in Summarist*, in Proceedings of the TIPSTER Workshop, Baltimore, Md., 1998). This generation function was not realized in the work upon which this paper was based.

The Knowledge Management (KM) system from SRA International, Inc. extracts summarization features using morphological analysis, name tagging, and co-reference resolution. The KM approach uses a machine-learning technique to determine the optimal combination of features in combination with statistical information from the corpus to identify the best sentences to include in a summary (http://www.SRA.com). The Cornell/Sabir system uses the document ranking and passage retrieval capabilities of the SMART text search engine to identify relevant passages in a document (C. Buckley et al., *The SMART/Empire TIPSTER IR System*, in Proceedings of TIPSTER Phase III Workshop, 1999). The text summarizer from CGI/CMU uses a technique called Maximal Marginal Relevance (MMR), which measures the relevance of each sentence in a document, both relative to a query as well as relative to sentences that have already been added to the summary. The MMR system then produces summaries of a document by identifying key relevant, non-redundant information found within the document (J. Goldstain et al., *Summarizing Text Documents: Sentence Selection and Evaluation Metrics*, in Proceedings of ACM SIGIR'99, Berkeley, Calif., August 1999).

Query-relevant text summaries such as those mentioned above may be useful for determining whether a given document is relevant to a user's query, and, if a document is relevant, for identifying which part of the document is related to the query. Since query-relevant summaries are created responsive to particular queries, however, these types of summaries do not provide an overall sense of the document content; consequently, query-relevant summaries are not appropriate for content overview. Generic text summarization techniques must be developed for identifying key topics within documents and for categorizing those documents.

SUMMARY OF THE INVENTION

The present invention provides two approaches to output high quality generic text summaries of predetermined or user-specified length. Briefly, the various inventive embodiments provide generic summarization of document content using relevance measurement technologies and latent semantic analysis techniques. Generic text summaries may be produced by ranking and extracting sentences from original documents; broad coverage of document content as well as decreased redundancy may simultaneously be achieved by constructing summaries from sentences that are highly ranked and different from each other.

In accordance with one aspect of the present invention, for example, conventional IR technologies may be applied in a unique way to perform the summarization. In one exemplary embodiment, three IR processes may be combined to ensure accurate summaries. An inventive system or method of text summarization may perform the following operations: measure the relevance between the document as a whole and each of its sentences; select the most relevant sentence in the context of the entire document; and eliminate all the terms contained in the selected sentence. These procedures of relevance measurement, sentence selection, and term elimination may be repeated in successive iterations until a predetermined number of sentences has been selected.

In accordance with another aspect of the present invention, for example, a "terms-by-sentences" matrix of the entire document may be created. A singular value decomposition technique may be applied to the terms-by-sentences matrix such that all the sentences from the document may be projected into the singular vector space. A system and method of generic text summary may then select the sentences having the largest index values with the most important singular vectors as part of the text summary.

The above-mentioned and other attendant advantages of the present invention will become more apparent upon examination of the following detailed description of the preferred embodiments thereof with reference to the attached drawing figures.

DETAILED DESCRIPTION OF THE PREFERRED EMBODIMENTS

Figure 1:
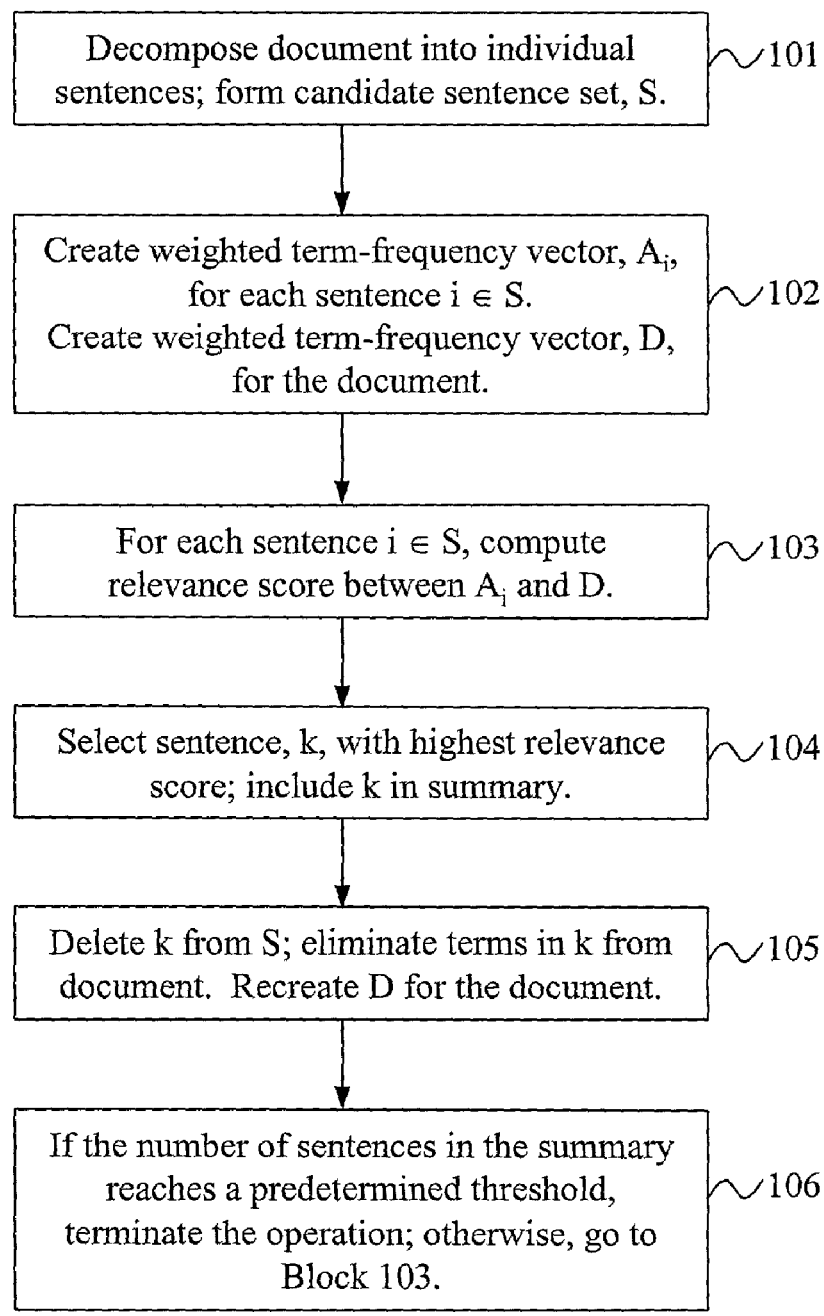
FIG. 1 is a simplified flow chart of the operation of one embodiment of a generic text summarization system and method.
Figure 2:
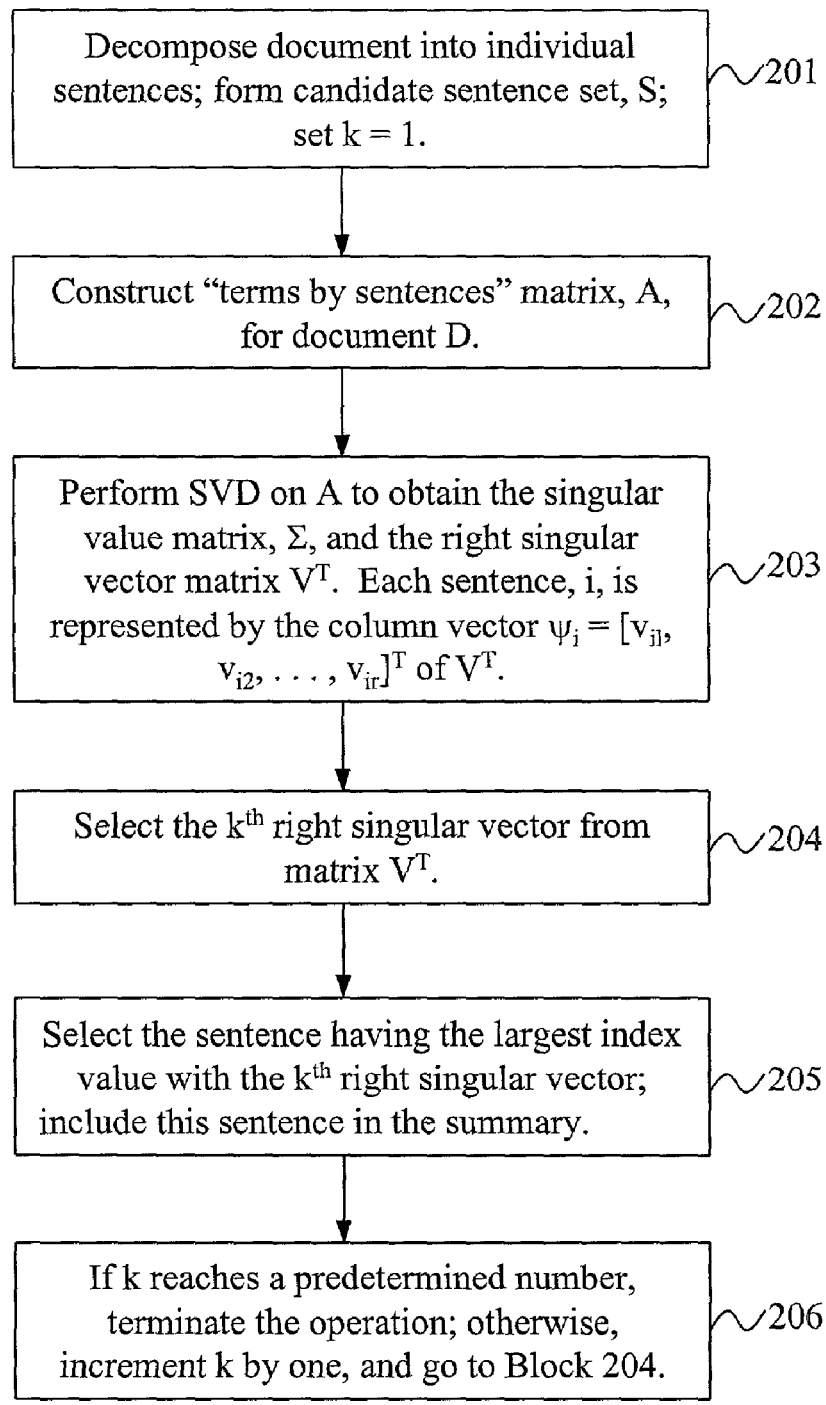
FIG. 2 is a simplified flow chart of the operation of another embodiment of a generic text summarization system and method.

With reference now to the drawings, FIG. 1 is a simplified flow chart of the operation of one embodiment of a generic text summarization system and method, and FIG. 2 is a simplified flow chart of the operation of another embodiment of a generic text summarization system and method.

By way of background, a document usually consists of several topics. Some topics are typically described in detail by more sentences than other topics, and hence may be inferred to comprise the major (or most important) content of the document. Other topics may be briefly mentioned to supplement or to support the major topics, or to make the whole story more complete. Those of skill in the art will appreciate that a good generic text summary should cover the major topics of the document as thoroughly as possible within a prescribed length (word count or sentence count, for example), while at the same time, minimizing redundancy.

A system and method of generic text summarization may advantageously decompose an entire document into a plurality of individual sentences; after such decomposition, a weighted term-frequency vector may be created for each sentence in the document as follows. A term-frequency vector, $T_i$, for a passage, i, may be expressed as $$T_i = [t_{1i}, t_{2i}, \ldots, t_{ni}]^t$$

where each element, $t_{ji}$, denotes the frequency with which a given term, j, occurs in the passage i. The passage i may represent an individual phrase, a sentence, a paragraph, or the entire document, for example.

Similarly, a weighted term-frequency vector, $A_i$, for the same passage may be expressed as $$A_i = [a_{1i}, a_{2i}, \ldots, a_{ni}]^t$$

where each element, $a_{ji}$, in the weighted term-frequency vector may further be defined as $$a_{ji} = L(t_{ji}) G(t_{ji}).$$

In the equation above, $L(t_{ji})$ represents a local weighting function for term j in passage i, and $G(t_{ji})$ represents a global weighting function for term j. During its creation, the weighted term-frequency vector $A_1$, may be normalized by its length $|A_i|$; accordingly, during subsequent computations, the system may employ either the original term-frequency vector $A_i$, or the normalized vector.

It will be appreciated by those of skill in the art that many possible weighting schemes exist for both the local weighting function $L(t_{ji})$ and the global weighting function $G(t_{ji})$. Different weighting schemes may influence the performance of a generic text summarization system and method; performance and accuracy may be maximized when both an appropriate local weighting function and an appropriate global weighting function are applied simultaneously.

By way of example only, and not by way of limitation, a local weighting function, L(i), may take one of the following four popular forms.

In a very simplistic, No Weight scheme: L(i)=tf(i), where tf(i) represents the number of times the term i occurs in a given sentence.

In a Binary Weight scheme: L(i)=1, if the term i appears at least once in a given sentence; otherwise, L(i)=0.

In an Augmented Weight scheme: $L(i)=0.5+0.5$ $(tf(i)/tf(max))$, where tf(max) represents the term-frequency of the most frequently occurring term in a sentence.

In a Logarithmic Weight scheme: $L(i)=\log(1+tf(i))$.

Also by way of example only, a global weighting function $G(i)$ may take one of the following two popular forms.

In a No Weight scheme: $G(i)=1$, for any given term i.

In an Inverse Document Weight scheme: $G(i)=\log(N/n(i))$, where N represents the total number of sentences in the document, and n(i) represents the number of sentences that contain the term i.

Additionally, as noted above, when a weighted term-frequency vector, $A_k$, of a sentence, k, is created using one of the local and one of the global weighting schemes noted above, for example, either the original form of $A_k$ may be used by the summarizer, or another vector may be created by normalizing $A_k$ by its length, or magnitude, $|A_i|$. In this exemplary embodiment with four possible local weighting functions, two possible global weighting functions, and the option of implementing the original or the normalized vector, 16 possible weighting schemes exist. It will be appreciated by those of skill in the art that other combinations and possibilities exist, with different approaches or strategies for local and global weighting.

Turning now to FIG. 1, an exemplary embodiment of a generic text summarizer may apply conventional IR technologies to create accurate and non-redundant summaries. First, a document may be decomposed into a plurality of individual sentences from which a candidate sentence set may be created (block 101). A weighted term-frequency vector as described above, for example, may be created for the entire document as a whole as well as for each sentence in the candidate sentence set (block 102). Next, a relevance score may be computed for each sentence in the candidate sentence set in accordance with relevance to the document as a whole, and the sentence with the highest relevance score may be selected as a sentence for inclusion in the summary (blocks 103 and 104).

Various techniques are known in the art for computing relevance scores for one vector relative to another vector. For example, at block 103, a method and system of generic text summarization may calculate the inner product (or dot product) of the weighted term-frequency vector for the sentence under consideration and the weighted term-frequency vector for the document.

The selected sentence may then be removed from the candidate sentence set, and all the terms contained in this selected sentence may be eliminated from the document (block 105). As shown in block 105, deletion of the sentence and elimination of that sentence's terms from the document generally requires that the weighted term-frequency vector for the document as a whole be reconstructed; this may ensure accuracy of subsequent relevancy computations.

As indicated at block 106, with respect to the remaining sentences, the relevance score computation (block 103), the sentence selection (block 104), and the term elimination (block 105) operations may be repeated until a predetermined number of sentences has been selected.

It will be appreciated by those of skill in the art that, at block 104 of the foregoing operation, the sentence, k, having the highest relevance score (relative to the document) may be considered the sentence that best represents the major content of the document. Therefore, selecting sentences based upon relevance scores in the foregoing manner may ensure that tie summary represents the major topics of the document to the greatest extent possible. On the other hand, eliminating all the terms contained in k from the document, as shown at block 105, may ensure that retrieval of the subsequent sentence (in the following iteration) with the highest relevance score will create minimum overlap with the subject matter contained in sentence k. In this manner, a very low level of redundancy may be achieved during creation of a summary that covers every major topic in the document.

In accordance with the latent semantic indexing approach illustrated in the FIG. 2 embodiment, a singular value decomposition (SVD) technique may be employed during creation of a generic text summary, as described in detail below. As indicated at block 201, this alternative embodiment may begin in the same manner as the FIG. 1 embodiment, namely, by decomposing a document into a plurality of individual sentences from which a candidate sentence set may be created.

By way of background, it should be appreciated that in order to implement SVD techniques during document summarization, a "terms-by-sentences" matrix may be constructed for the document (block 202). A terms-by-sentences matrix may be in the form $$A=[A_1, A_2, \ldots, A_n]$$

where each column vector $A_i$ represents the weighted term-frequency vector of a sentence, i, in the document under consideration. If there are a total of m terms and n sentences in the document, then the terms-by-sentences matrix A for the entire document will have dimensions of m×n. Since every word does not normally appear in each sentence, the matrix A is usually sparse. In practice, local and global weightings such as described above may be applied to increase or to decrease the importance of terms within a particular sentence or among sentences, as is known in the art (see, e.g., S. Dumais, *Improving The Retrieval of Information From External Sources*, Behavior Research Methods, Instruments, and Computers, vol. 23, 1991).

Given a matrix, A, of dimensions m×n, where without loss of generality m≧n, the SVD of A is defined as follows (see, W. Press et al., *Numerical Recipes in C: The Art of Scientific Computing*, Cambridge, England: Cambridge University Press, 2 ed., 1992):

$$A=U\Sigma V^T$$

In the equation above: $U=[u_{ij}]$ is an m×n column-orthonormal matrix whose columns are called left singular vectors; $\Sigma=\text{diag}(\sigma_1, \sigma_2, \ldots, \sigma_n)$ is an n×n diagonal matrix whose diagonal elements are non-negative singular values sorted in descending order; $V=[v_{ij}]$ is an n×n orthonormal matrix whose columns are called right singular vectors; and $V^T$ is the transpose of V. If rank (A)=r, then $\Sigma$ satisfies the following relationship:

$$\sigma_1 \geq \sigma_2 \geq \ldots \sigma_r \geq \sigma_{r+1} = \ldots = \sigma_n = 0$$

This application of SVD techniques to the matrix A may be interpreted from two different perspectives. From a transformation point of view, the SVD derives a mapping between the m-dimensional space spanned by the weighted term-frequency vectors and the r-dimensional singular vector space with all of its axes linearly-independent. This mapping projects each column vector in matrix A (which represents the weighted term-frequency vector of sentence i), to column vector $\psi_i=[v_{i1}, v_{i2}, \ldots, v_{ir}]^T$ of matrix $V^T$, and maps each row vector in matrix A (which represents the occurrence count of the term, j, in each of the documents), to row vector $\phi_j=[u_{j1}, u_{j2}, \ldots, u_{jr}]$ of matrix U. Here, each element, $v_{ix}$ of $\psi_i$, $u_{jy}$ of $\phi_j$, is called the index with the $i^{th}$, $j^{th}$ singular vectors, respectively.

From a semantic point of view, the SVD technique may enable the summarizer to derive the latent semantic structure of the document represented by the matrix A (see, e.g., S. Deerwester et al., *Indexing By Latent Semantic Analysis*, Journal of the American Society for Information Science, vol. 41, pp. 391-407, 1990). This operation may reflect a breakdown of the original document into a number, r, of linearly-independent base vectors or concepts. Each term and sentence from the document may be jointly indexed by these base vectors and concepts. A unique SVD feature which is lacking in conventional IR technologies is that the SVD may generally be capable of capturing and modeling the interrelationships among terms such that semantic clusters of terms and sentences may be created.

By way of example, consider the words "doctor", "physician", "hospital", "medicine", and "nurse". The words "doctor" and "physician" may be used synonymously in many circumstances, while "hospital", "medicine", and "nurse" may represent closely related concepts. The two synonyms, doctor and physician, will often appear with many of the same related words such as hospital, medicine, nurse, and so forth. Given such similar or predictable patterns of word combinations, the words doctor and physician may be mapped near to each other in the r-dimensional singular vector space.

Furthermore, (as illustrated by M. Berry et al., *Using Linear Algebra For Intelligent Information Retrieval*, Tech. Rep. UT-CS-94-270, University of Tennessee, Computer Science Department, December 1994), if a word or sentence, W, has a large index value with an important singular vector, then W is very likely to represent a major or important topic or concept of the document as a whole. Other words or sentences which are closely related to W may advantageously be mapped close to W, and along the same singular vector as W in the space. In other words, each singular vector from the SVD may be interpreted as representing an identifiable, salient concept or topic in the document, and the magnitude of its corresponding singular value may represent the degree of importance of that salient topic.

Returning now to FIG. 2, the operation of an exemplary embodiment of an SVD-based document summarizer may proceed substantially as follows. First, as noted above, a document may be decomposed into a plurality of individual sentences from which a candidate sentence set may be created (block 201); additionally, a sentence counter variable, k, may be initialized at k=1. After document decomposition, a terms-by-sentences matrix, A (as described above, for example), may be created for the entire document (block 202). Creation of the terms-by-sentences matrix may advantageously employ both local and global weighting functions for each term in the document.

Next, as indicated at block 203, the SVD may be performed on A in order to obtain the singular value matrix, $\Sigma$, and the right singular vector matrix, $V^T$. Each sentence, i, may be represented by the column vector $\psi_i=[v_{i1}, v_{i2}, \ldots, v_{ir}]^T$ of $V^T$. The system may then select the $k^{th}$ right singular vector from matrix $V^T$, which is equivalent to selecting the $k^{th}$ row of $V^T$ (block 204).

In this embodiment, the sentence having the largest index value with the $k^{th}$ right singular vector may then be selected as a relevant sentence and included in the summary (block 205). Finally, as indicated at block 206, if the sentence counter variable, k, reaches a predetermined number, the operation may be terminated; otherwise, k may be incremented by one, and the system may revert to Block 204 for the next iteration.

At block 205 in FIG. 2, identifying the sentence having the largest index value on the $k^{th}$ right singular vector may be equivalent to finding the column vector $\psi_i$ whose $k^{th}$ element $v_{ik}$ is the largest. This operation may generally be equivalent to finding the sentence describing the salient topic represented by the $k^{th}$ singular vector. Since the singular vectors are sorted in descending order of their singular values, the $k^{th}$ singular vector represents the $k^{th}$ important topic. Because all the singular vectors are independent of each other, the sentences selected in accordance with this technique may contain the minimum redundancy.

From the foregoing, it can be seen that the present invention provides accurate generic text summaries of a desired length while minimizing redundancy and making efficient use of system resources. The preferred embodiments disclosed herein have been described and illustrated by way of example only, and not by way of limitation; it will be apparent to those of skill in the art that numerous modifications may be made thereto without departing from the spirit and scope of the invention.

What is claimed is:

1. A method of creating a generic text summary of a document; said method comprising:
   obtaining the document;
   creating a weighted document term-frequency vector for said document;
   for each sentence in said document, creating a weighted sentence term-frequency vector;
   computing a score for each said weighted sentence term-frequency vector in accordance with relevance to said weighted document term-frequency vector;
   selecting a sentence for inclusion in said generic text summary in accordance with said computing, wherein the selected sentence has the computed score representing high degree of relevance of the corresponding weighted sentence term-frequency vector to said weighted document term-frequency vector;
   deleting said selected sentence from said document and eliminating terms in said selected sentence from said document; and
   generating the generic text summary based on the selected sentence.

2. The method of claim 1 further comprising:
   recreating said weighted document term-frequency vector in accordance with said deleting and said eliminating; and
   selectively repeating said computing, said selecting, said deleting, said eliminating, and said recreating.

3. The method of claim 2 wherein said selectively repeating is terminated when a predetermined number of sentences has been selected.

4. The method of claim 1 wherein said computing comprises calculating an inner product of said weighted sentence term-frequency vector and said weighted document term-frequency vector.

5. The method of claim 1 wherein said creating a weighted sentence term-frequency vector comprises implementing a local weighting function and implementing a global weighting function.

6. The method of claim 5 wherein said creating a weighted sentence term-frequency vector comprises normalizing each said weighted sentence term-frequency vector by dividing the weighted sentence term-frequency vector by a magnitude of the weighted sentence term-frequency vector.

7. The method of claim 1 wherein said creating a weighted document term-frequency vector comprises implementing a local weighting function and implementing a global weighting function.

8. The method of claim 7 wherein said creating a weighted document term-frequency vector comprises normalizing said weighted document term-frequency vector by dividing the weighted document term-frequency vector by a magnitude of the weighted document term-frequency vector.

9. A system for creating a generic text summary of a document; said system comprising:
- a computer comprising at least a CPU and a memory;
- an interface for obtaining the document;
- a display for displaying said generic text summary; and
- summarizer program code, operable on said computer, for analyzing and summarizing said document; said summarizer program code comprising:
  - a vector generator for creating a weighted document term-frequency vector for said document and creating a weighted sentence term-frequency vector for each sentence in said document;
  - a scoring engine for computing a score for each said weighted sentence term-frequency vector in accordance with relevance to said weighted document term-frequency vector;
  - a selector for selecting a sentence for inclusion in said generic text summary in accordance with output results from said scoring engine;
  - a document editor for deleting said selected sentence from said document and for eliminating terms in said selected sentence from said document and;
  - a generic summary generator for generating the generic text summary based on the selected sentence.

10. The system of claim 9 wherein said vector generator recreates said weighted document term-frequency vector in accordance with output results from said document editor.

11. The system of claim 10 wherein said summarizer further comprises a loop routine for generating iterative sequential operations of said vector generator, said scoring engine, said selector, and said document editor.

12. The system of claim 11 wherein said loop routine is responsive to a predetermined limit such that said generic text summary is of a predetermined number of sentences.

13. A method of creating a generic text summary of a document; said method comprising:
- obtaining the document;
- decomposing said document into individual sentences;
- forming a candidate sentence set from said individual sentences;
- for each of said individual sentences in said candidate sentence set, creating a weighted sentence term-frequency vector;
- creating a weighted document term-frequency vector for said document;
- for each of said individual sentences in said candidate sentence set, computing a relevance score for said weighted sentence term-frequency vector relative to said weighted document term-frequency vector;
- selecting a sentence for inclusion in said generic text summary in accordance with said computing, wherein the selected sentence has the computed relevance score representing a high degree of relevance of the corresponding weighted sentence term-frequency vector to said weighted document term-frequency vector;
- deleting said selected sentence from said candidate sentence set;
- eliminating terms in said selected sentence from said document;
- recreating said weighted document term-frequency vector in accordance with said deleting and said eliminating; and
- generating the generic text summary based on the selected sentence.

14. The method of claim 13 further comprising: selectively repeating said computing, said selecting, said deleting, said eliminating, and said recreating.

15. The method of claim 14 wherein said selectively repeating is terminated when a predetermined number of sentences has been selected.

16. The method of claim 13 wherein said computing comprises calculating an inner product of said weighted sentence term-frequency vector and said weighted document term-frequency vector.

17. The method of claim 13 wherein said creating a weighted sentence term-frequency vector comprises implementing a local weighting function and implementing a global weighting function.

18. The method of claim 17 wherein said creating a weighted sentence term-frequency vector comprises normalizing each said weighted sentence term-frequency vector by dividing the weighted sentence term-frequency vector by a magnitude of the weighted sentence term-frequency vector.

19. The method of claim 13 wherein said creating a weighted document term-frequency vector comprises implementing a local weighting function and implementing a global weighting function.

20. The method of claim 19 wherein said creating a weighted document term-frequency vector comprises normalizing said weighted document term-frequency vector by dividing the weighted document term-frequency vector by a magnitude of the weighted document term-frequency vector.

* * * * *